(12) United States Patent
Janson et al.

(10) Patent No.: US 10,675,327 B2
(45) Date of Patent: Jun. 9, 2020

(54) APPLICATIONS OF MUSSEL ADHESIVE PROTEIN PRODUCT IN TREATMENT AND PREVENTION OF DISEASES RELATED TO MELANIN

(71) Applicant: JIANGYIN BENGT I. SAMUELSSON INSTITUTE OF LIFE SCIENCE CO., LTD., Jiangyin, Jiangsu (CN)

(72) Inventors: Jan Christer Janson, Uppsala (SE); Min Gao, Jiangsu (CN)

(73) Assignee: JIANGYIN BENGT I. SAMUELSSON INSTITUTE OF LIFE SCIENCE CO., LTD., Jiangyin, Jiangsu (CN)

( * ) Notice: Subject to any disclaimer, the term of this patent is extended or adjusted under 35 U.S.C. 154(b) by 0 days.

(21) Appl. No.: 15/742,969

(22) PCT Filed: Jul. 20, 2015

(86) PCT No.: PCT/CN2015/084494
§ 371 (c)(1),
(2) Date: Jan. 9, 2018

(87) PCT Pub. No.: WO2017/011984
PCT Pub. Date: Jan. 26, 2017

(65) Prior Publication Data
US 2018/0221444 A1  Aug. 9, 2018

(51) Int. Cl.
| | |
|---|---|
| A61K 38/17 | (2006.01) |
| A61K 9/06 | (2006.01) |
| A61K 9/12 | (2006.01) |
| A61K 8/00 | (2006.01) |
| A61P 17/00 | (2006.01) |
| A61K 35/618 | (2015.01) |
| A61K 8/64 | (2006.01) |
| A61K 9/00 | (2006.01) |
| A61Q 19/02 | (2006.01) |
| A61K 38/48 | (2006.01) |

(52) U.S. Cl.
CPC ............ *A61K 38/1767* (2013.01); *A61K 8/00* (2013.01); *A61K 8/64* (2013.01); *A61K 9/0014* (2013.01); *A61K 9/06* (2013.01); *A61K 9/12* (2013.01); *A61K 35/618* (2013.01); *A61K 38/17* (2013.01); *A61P 17/00* (2018.01); *A61Q 19/02* (2013.01); *A61K 38/4826* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 6,395,269 B1 * | 5/2002 | Fuller | ............ A61K 8/046 424/400 |
| 10,485,848 B2 | 11/2019 | Gao | |
| 10,568,938 B2 | 2/2020 | Samuelsson et al. | |
| 2002/0018787 A1 | 2/2002 | Kendall et al. | |
| 2002/0168416 A1 | 11/2002 | Mitra et al. | |
| 2002/0187201 A1 | 12/2002 | Bhonde et al. | |
| 2003/0044470 A1 | 3/2003 | Wani et al. | |
| 2005/0159396 A1 | 7/2005 | Harty | |
| 2006/0275218 A1 | 12/2006 | Tamarkin et al. | |
| 2006/0275370 A1 | 12/2006 | Chung et al. | |
| 2013/0052712 A1 | 2/2013 | Cha et al. | |
| 2018/0228873 A1 | 8/2018 | Samuelsson et al. | |
| 2018/0243371 A1 | 8/2018 | Gao et al. | |
| 2020/0101135 A1 | 4/2020 | Gao et al. | |

FOREIGN PATENT DOCUMENTS

| | | |
|---|---|---|
| CN | 1112831 A | 12/1995 |
| CN | 101348518 A | 1/2009 |
| CN | 101348520 A | 1/2009 |
| CN | 101585874 A | 11/2009 |
| CN | 101991840 A | 3/2011 |
| CN | 102302417 A | 1/2012 |
| CN | 103520766 A | 1/2014 |
| CN | 104323927 A | 2/2015 |
| CN | 104645313 A | 5/2015 |
| CN | 104645320 A | 5/2015 |
| CN | 104857552 A | 8/2015 |
| EP | 2471819 A2 | 7/2012 |
| GB | 2347349 A | 9/2000 |
| KR | 20110132498 A | 12/2011 |
| RU | 2043109 C1 | 9/1995 |
| WO | 92/21354 | 12/1992 |
| WO | 99/64580 | 12/1999 |
| WO | 00/71140 A2 | 11/2000 |
| WO | 01/05411 A1 | 1/2001 |
| WO | 2013/143077 A1 | 10/2013 |
| WO | 2014/186937 A1 | 11/2014 |

OTHER PUBLICATIONS

Burzio, "Cross-Linking in Adhesive Quinoproteins: Studies with Model Decapeptides," Biochem: 39, 11147-11153 (2009) (Year: 2009).*
Bandara et al., "Marine mussel adhesion: biochemistry, mechanisms, and biomimetics," J. Adhesion Sci. Tech. 27:2139-2162 (2012) (Year: 2012).*
Gupta et al., "The treatment of melasma: A review of clinical trials," J. Amer. Acad. Dermatol. 55:1048-1065 (2006) (Year: 2006).*

(Continued)

*Primary Examiner* — Julie Ha
*Assistant Examiner* — Kristina M Hellman
(74) *Attorney, Agent, or Firm* — Pepper Hamilton LLP

(57) ABSTRACT

Disclosed are applications of a mussel adhesive protein or preparations thereof in treatment and prevention of diseases related to melanin. Specifically disclosed are applications of a mussel adhesive protein or preparations thereof in treatment and prevention of pigmentations such as chloasma, freckles, melanosis, applications in skin cancers represented by melanoma, and applications in treatment of pigmentation possibly caused by skin diseases or drugs.

16 Claims, No Drawings

(56) References Cited

OTHER PUBLICATIONS

Slominski et al., "Melanin Pigmentation in Mammalian Skin and Its Hormonal Regulation," Physiol. Rev. 84: 1155-1228 (2004) (Year: 2004).*
Sklar et al., "Effects of ultraviolet radiation, visible light, and infrared radiation on erythema and pigmentation: a review," Photochem. Photobiol. Sci. 12:54-64 (2013) (Year: 2013).*
International Search Report and Written Opinion for corresponding Application PCT/CN2015/084494 (dated Apr. 26, 2016).
Zhu et al., "The Research Progress on Mussel Adhesive Proteins," Advances in Marine Science 32(4):560-570 (2014).
Gao et al., "Review on Mussel Adhesive Protein," J. Anhui Agri. Sci. 39(32):19860-19862 (2011).
U.S. Appl. No. 15/742,969, filed Jan. 9, 2018, First Named Inventor: Samuelsson.
U.S. Appl. No. 15/751,551, filed Feb. 9, 2018, First Named Inventor: Min Gao.
Wang et al., "Research Progress of Mussel Adhesive Proteins and its Derivatives Dopamine," Development and Application of Materials 29:101-104 (2014).
Yan et al., "Dopamine Controls Systemic Inflammation through Inhibition of NLRP3 Inflammasone," Cell 160:62-73 (2015).
Fei et al, "Application of MAP after Treatment of Atrophic Acne Scars with Micro-Plasma," J. Clin. Dermatol. 44(1):40-42 (2015).
Kaushik et al., "Biomedical and Clinical Importance of Mussel-Inspired Polymers and Materials," Mar. Drugs 13:6792-6817 (2015).
Li et al., "Progress of Research on Pharmaceutical Values of Mussels," Fisheries Science 23(11):43-44 (2004).
Liu et al., "Cytotoxicty Tests for the Mussel Adhesive Protein Dressing for Wound Healing," Chinese Journal of Tissue Engineering Research 17(38):6785-6790 (2013).
Wang et al., "The Mechanism of Adhesion and Film Forming and their Applied Research Progress of Mussel Adhesion Proteins," J. Functional Mat. 14:14013-14020 (2014).
U.S. Appl. No. 15/742,960, filed Jan. 9, 2018, First Named Inventor: Samuelsson.
Rainsford & Whitehouse, "Gastroprotective and Anti-Inflammatory Properties of Green Lipped Mussel (Perna canaliculus) Preparation," Arzneimittelforschung 30(12):2128-32 (1980) (abstract).
International Search Report and Written Opinion for International Application No. PCT/CN2016/095364 (dated Oct. 8, 2016) (English translation of International Search Report only).
International Search Report and Written Opinion for International Application No. PCT/CN2015/087011 (dated May 20, 2016) (English translation of International Search Report only).
Couch et al., "Anti-Inflammatory Activity in Fractionated Extracts of the Green-Lipped Mussel," The New Zealand Medical Journal 95(720):803-806 (1982).
Park et al., "Antioxidant and Anti-Inflammatory Activities of Protein Hydrolysates from Mytilus Edulis and Ultrafiltration Membrane Fractions," J. Food Biochem. 38:460-468 (2014).
International Search Report and Written Opinion for International Application PCT/CN2015/084492 (dated Apr. 26, 2016).
Kim et al., "Mussel-Mimetic Protein-Based Adhesive Hydrogel," Biomacromolecules 15:1579-1585 (2014).
Wang et al., "Purification and Characterisation of a Novel Antioxidant Peptide Derived from Blue Mussel (Mytilus Edulis) Protein Hydrolysate," Food Chem. 138:1713-1719 (2013).
Kim et al., "Mussel-Mimetic Protein-Based Adhesive Hydrogel," Amer. Chem. Soc. 15:1579-1585 (2014).
Kim et al., "Purification of a Novel Anticancer Peptide from Enzymatic Hydrolysate of Mytilus Coruscus." J. Microbiol. Biotechnol. 22(10): 1381-1387 (2012).
Nichols et al., "Skin Photoprotection by Natural Polyphenols: Anti-Inflammatory, Antioxidant and DNA Repair Mechanisms," Arch. Dermatol. Res. 302:71-83 (2010).

* cited by examiner

APPLICATIONS OF MUSSEL ADHESIVE PROTEIN PRODUCT IN TREATMENT AND PREVENTION OF DISEASES RELATED TO MELANIN

This application is a national stage application under 35 U.S.C. § 371 which claims priority of PCT Application No. PCT/CN2015/084494, filed Jul. 20, 2015.

FIELD OF THE INVENTION

The present invention substantially relates to the technical field of drugs, cosmetics, medical products, disinfecting products, healthcare products, food, and household chemicals, and more specifically, relates to a mussel adhesive protein product and a use thereof for treating and preventing melanin-related diseases.

DESCRIPTION OF THE RELATED ART

Melanin is a black-brown pigment that exists in animal skin or hair, which is produced by a special cell, i.e. melanocyte, and stored therein. Melanin exists extensively in human skin, mucosa, retinal, cerebral leptomeninges, gallbladders and ovaries. Skin has its color just because of the presence of melanin. Melanin is a biological pigment, which is formed by tyrosine or 3,4-dihydroxyphenylalanine through a series of chemical reactions, and is usually present in a polymerized manner.

Melanin is essentially a protein. It exists among the skin basal layer cells (also referred to as "chromatoblasts"), which is a substance referred to as "melanin primary matter." Chromatoblasts secrete melanin pigment. When UV (UVA and UVB) irradiates on skin, UVB acts on the skin basal layer, and the skin will be in a "self defense" state to stimulate melanin pigment through UV, and to activate tyrosinase, thereby protecting skin cells. Dopa is a precursor of melanin, formed through oxidation of tyrosine and then releases melanin. Through layer-by-layer migration of cell metabolism, melanin reaches the epidermal layer of the skin to form freckles, sunburns, black spots, and other shapes.

The production of melanin is often related to endocrine disorders and solar irradiation. The quantity of melanocytes is mainly subjected to heredity, also related to endocrine hormones and nutrition. Diseases caused by melanin, such as freckles, chloasma, melanosis and other chromatosis diseases, are topics that have been extensively studied in the beauty community.

Inhibition of pigments during the production process thereof is different from treatment of the produced pigments. To inhibit chromatosis, the process from tyrosine to dopa, then to dihydroxy indole, until the formation of melanin should be interrupted. In such a process, inflammations may be inhibited to prevent the production of inflammatory factors and thereby realize the pigment inhibition; alternatively, the production of pigments can be blocked through a substance capable of reacting with substances in the process of pigment formation; alternatively, the production of pigments can be prevented through oxidation resistance. On the other hand, pigment treatment is to make formed melanin to decompose through a reducing substance, such that the pigment disappears in the end.

Mussel adhesive protein (MAP), also known as *Mytilus edulis* foot protein (Mefp), is a special protein secreted by marine shellfish, such as *Mytilus edulis* Linnaeus, *Mytilus coruscus* and *Perna viridis*. Mussels are typically attached, in groups, to coastal reefs or ship bottom and have the ability to resist wave impacts in coastal waters. In fact, mussels can be extremely firmly attached to a base of almost any material, such as metals, wood, glass, etc. The main reason why mussels have the above characteristic is that such a special adhesive protein can be produced and stored inside the byssus gland thereof. Mussels release the adhesive protein through byssus to a surface of a solid like rock, to form a water-proof bonding and consequently fix themselves.

At present, 11 adhesive protein subtypes have been identified in mussels, including mefp-1, mefp-2, mefp-3, mefp-4, mefp-5, mefp-6, the collagens pre-COL-P, pre-COL-D, pre-COL-NG, and the mussel feet matrix proteins PTMP and DTMP (Yaoyao Zhu, et al., Advances in Marine Science, 2014, 32(4): 560-568). MAP has two structural characteristics: (1) comprising lysine, such that the protein carries a high loading of positive charge; (2) comprising 3,4-dihydroxyphenylalanine (DOPA, Levodopa). Human cells and tissues carry negative charges. MAP is tightly bonded to the cells and tissues through the static interaction between its own positive charge and the negative charge of the human cells and tissues, thereby playing a role of protection and treatment. In addition, DOPA is oxidized to produce o-diquinone, which may be crosslinked with unoxidized DOPA to form a membrane or a reticular support, such that the proteins are attached to the human body surface in a tighter and firmer manner to play a protective role. MAP is a macromolecular protein, and it needs about 3-10 days to be completely degraded in human body. It has superior ability to be attached to cells and tissues, such that MAP is stable in a local part to continuously play its role.

Despite the above characteristics of MAP, MAP products are applied in a very limited number of fields at present. Commercial MAP products include Cell-Tak by BD Biosciences from the U.S., MAP Trix by Kollodis from South Korea, and Hydrogel by Biopolymer from Sweden. These products are either directly used as an MAP solution or stored as a freeze-dried powder and dissolved prior to use. Their applications are mainly limited to micro-cellular bonding and tissue bonding agents. There are also reports that MAP is used for fetal membrane repair, seawater corrosion-resistant coating, cardiac drug carrier, etc.

SUMMARY OF THE INVENTION

The inventors find that MAP is a polyphenolic protein, and the dopa group contained in its molecule is an important substance participating in the synthesis of melanin. In diseases caused by melanin, such as chloasma, freckles, and melanosis, the dopa group in the MAP molecule can enhance the activity of tyrosinase and then impact the secretion of melanin, thereby achieving the goal of treating and preventing melanin-related diseases.

The inventors find that the molecular weight of MAP reaches up to 100 kD, and the absorption rate is low during direct percutaneous use, hence affecting the action effect. The efficiency of percutaneous action can be improved by forming micro wounds on the skin surface or adding enzymes to hydrolyze MAP, to more effectively treat chloasma, freckles, melanosis, and other chromatosis skin diseases, effectively inhibit skin cancers with melanoma as a representative, and prevent chromatosis that is potentially caused by exposure to the sun or skin diseases like acne.

One object of the present invention is to provide an MAP product.

MAP used herein refers to one or a mixture of several selected from the group consisting of 11 MAP subtypes, including mefp-1, mefp-2, mefp-3, mefp-4, mefp-5, mefp-6, the collagens pre-COL-P, pre-COL-D, pre-COL-NG, and the mussel feet matrix proteins PTMP and DTMP, that are currently known and purified from marine mussels, such as *Mytilus edulis* Linnaeus, *Mytilus coruscus*, and *Perna viridis*, in bivalve mollusks of Mytilidae. MAP used herein may have a pH value, in an aqueous solution, in a range of pH 1.0-7.0, and in particular, in a range of pH 3.0-6.5 for better therapeutic results thereof.

MAP used herein may be obtained using the following preparation methods, for example, a method for separating and purifying MAP by using mixed adsorption chromatography according to Chinese Patent no. ZL200710179491.0, a method for purifying MAP by using carboxymethyl ion exchange chromatography according to Chinese Patent no. ZL200710179492.5, and a method for separating and purifying MAP by using salting out and dialysis according to Chinese Patent no. ZL200910087567.6.

MAP used herein may be in a form of solution or freeze-dried powder, and in particular, the MAP concentration in a product may be 0.1-15.0 mg/mL. When the concentration is overly low, MAP does not have a good effect, and when the concentration is overly high, it may cause cytotoxicity, skin irritation, etc., which is not favorable for treatment of skin melanin.

MAP used herein may also be combined with excipients to prepare a liquid formulation. An exemplary MAP liquid formulation is prepared by dissolving or diluting an MAP stock solution or freeze-dried powder to a certain concentration or pH value, and the solution used for dissolution or dilution could be water, physiological saline, phosphate solution, acetate solution, borate solution, etc. MAP in the final product may have a pH value in a range of pH 1.0-7.0, and in particular, in a range of pH 3.0-6.5 for better therapeutic results thereof.

MAP used herein may also be combined with excipients to prepare a gel formulation. An exemplary MAP gel formulation is prepared by mixing an MAP solution or freeze-dried powder with a gel matrix material, and the gel matrix material may be one or any combination of cellulose derivatives, carbomer and alginates, gummi tragacanthae, gelatin, pectin, carrageenan, gellan gum, starch, xanthan gum, cationic guar gum, agar, noncellulosic polysaccharides, vinyl polymers, acrylic resins, polyvinyl alcohol and carboxyvinyl polymer.

MAP used herein may also be combined with excipients to prepare a lotion. An exemplary MAP lotion is made by mixing an MAP solution or freeze-dried powder with a lotion matrix; said lotion matrix may comprise one or any combination of cellulose derivatives, glycerin, noncellulosic polysaccharides, and propanediol.

MAP used herein may also be combined with excipients to prepare a paste. An exemplary MAP paste is made by mixing MAP with a paste matrix material; said paste matrix material may comprise glycerin, vaseline, paraffin, etc.

MAP used herein may further be combined with a matrix material to prepare a dressing or a therapy patch for application on a skin surface. The liquid in an exemplary MAP therapy patch may be an MAP solution or a combination thereof with one or more of cellulose derivatives, carbomer and alginates, gummi tragacanthae, gelatin, pectin, carrageenan, gellan gum, starch, xanthan gum, cationic guar gum, agar, noncellulosic polysaccharides, vinyl polymers, acrylic resins, polyvinyl alcohol or carboxyvinyl polymer, gelatin, isinglass, pectin, alginates, glycerin, vaseline, paraffin, polyethylene glycol, vitamins, and glutathione. The above MAP solution or composition impregnates a matrix material, such as gauze, non-woven cloth, or silk paper, and the therapy patch may be, for example, Band-Aid, facial mask, eye mask, hand mask, foot mask, etc.

Components known in the art to be capable of strengthening moisturizing and anti-oxidation capabilities, such as glycerin, polyethylene glycol, vitamins, and glutathione, may be further added into the above various formulations that contain MAP to further improve the moisturizing and anti-oxidation capabilities thereof.

Components such as amino acids, collagen and hyaluronic acid, and extracts from aloe, grape seed, tea leaves, ginseng, and snails, may be further added into the above various formulations that contain MAP to improve the capabilities thereof nourishing skin and accessory organs to the skin, and to improve the tenderness thereof.

All the above formulations may be prepared with methods known in the art, and reference may be made to, for example, "Pharmaceutical Preparation", for detailed operating steps.

MAP used herein may be used as a main raw material to prepare a drug along with a pharmaceutically acceptable carrier. The drug may be a liquid formulation, a gel formulation, a lotion, a paste, a therapy patch, or a foam formulation. The drug may be applied externally, and in particular, may be applied on the skin externally.

MAP used herein may be used as a main raw material to prepare a medical device. The term used herein, medical device, refers to a material or other similar or related objects used, directly or indirectly, on the human body. The medical device may be a liquid formulation, a gel formulation, a lotion, a paste, a therapy patch, or a foam formulation. The medical device may be applied externally, and in particular, may be applied on the skin externally.

MAP used herein may be used as a main raw material to prepare cosmetics along with excipients that are acceptable in the field of cosmetics. The cosmetics may be a liquid formulation, a gel formulation, a lotion, a paste, a therapy patch, or a foam formulation. The cosmetics may be applied externally, and in particular, may be applied on the skin externally.

MAP used herein may be used as a main raw material to prepare a disinfecting product along with excipients that are acceptable in the field of disinfecting products. The term used herein, disinfecting product, refers to a disinfectant, a disinfecting device, a sanitary product and a disposable medical article that kills or eliminates pathogenic microorganisms in the environment in a chemical, physical or biological manner. The disinfecting product may be a liquid formulation, a gel formulation, a lotion, a paste, a therapy patch, or a foam formulation. The disinfecting product may be applied externally, and in particular, may be applied on the skin externally.

MAP used herein may be used as a main raw material to prepare a healthcare product or food along with excipients that are acceptable in the field of healthcare products or foods. The healthcare product or food may be a liquid formulation, a gel formulation, a lotion, a paste, a therapy patch, or a foam formulation. The healthcare product or food may be applied externally or edible, and in particular, may be applied on the skin externally.

MAP used herein may be used as a main raw material to prepare a household chemical along with excipients that are acceptable in the field of household chemicals. The term used herein, household chemicals, refers to a chemical product for daily use, including shampoo, bath gel, etc. The household chemical may be a liquid formulation, a gel formulation, a lotion, a paste, a therapy patch, or a foam formulation. The household chemical may be applied externally, and in particular, may be applied on the skin externally.

Another object of the present invention is to provide a use of MAP products in treating and preventing melanin pigmentation. In particular, a use is provided to treat diseases of chromatosis, such as chloasma, freckles, and melanosis, inhibit skin cancers with melanoma as a representative, and prevent chromatosis that is potentially caused by exposure to the sun or skin diseases like acne.

The term used herein, treat, refers to a process that intervenes or changes a specific health state and activities taken to relieve suffering. The term used herein, inhibit, refers to a process that mitigates the original damages after a tissue or organism is irritated.

The term used herein, prevent, refers to the preparation of a solution in advance for situations in which potential deviation from subjectively expected track or objective universal laws occurs during disease treatment, so as to avoid the occurrence of potential damage.

Chloasma refers to facial pigmentation of yellowish-brown pigment. It is mostly spread in a symmetric butterfly shape on the chin.

Freckle refers to yellowish-brown pigmentation dots on facial skin, which belongs to autosomal dominant inheritance. It tends to occur on the face, in particular the nose and two cheeks, and may affect exposed positions like neck, shoulders, and backs of hands. There is no rash on positions that are not exposed. The damage is rashes that are light brown or dark brown, from needle tip to green bean in size, and of a round, oval or irregular shape. They are dispersed or distributed in groups, isolated and not combined.

With respect to melanosis, workers develop chronic skin inflammations due to long-term contact with bitumen, coal tar, and petroleum products, or due to long-term inhalation of volatilized matter from these substances, and ultimately develop pigmentation on the skin.

Melanoma is a tumor caused by melanocytes of the skin and other organs. Skin melanoma has the manifestation that pigmented skin lesions undergo significant changes over several months or several years.

Chromatosis caused by skin diseases is caused by inflammatory skin diseases or by various drugs. For example, pigmentation happens after treatment of solar dermatitis or acne. Lichen planus and lichen planus-like drug eruptions lead to pigmentation. Fixed drug eruptions can leave characteristic ring-shaped pigmentation blemishes. Drugs that can cause pigmentation include amiodarone, tetracycline, minocycline, bleomycin, cyclophosphamide, antimalarial drugs like chloroquine and quinine, chlorpromazine and other phenothiazine drugs that can cause grey-blue pigmentation of the skin at exposed areas.

According to one aspect of the present invention, MAP can be used independently to treat and prevent melanin pigmentation. When MAP is used independently to treat and prevent melanin pigmentation, it can be used directly or after a micro wound surface is created. Methods to create a micro wound surface include: micro-needle (which can be made of silicon, silicon dioxide, cellulose, etc.), rolling needle (which can be made of stainless steel, titanium, polytetrafluoroethylene, etc.), laser (e.g. fractional laser).

According to another aspect of the present invention, MAP can be combined with an enzyme for use after enzymolysis, wherein, MAP inhibits the oxidation process that forms melanin, and combines with dopa (3,4-dihydroxyphenylalanine) in the melanin formation process to interrupt the further formation process of the pigment. In addition, as the molecular weight of MAP is high, the percutaneous administration is difficult, and the utilization rate is low, the application of enzymolysis of MAP improves the percutaneous administration efficiency and enhances the therapeutic effect.

The enzyme used herein may be: (1) trypsin from various sources, for example, trypsin extracted from cod pancreas, bull pancreas, pig pancreas, and euphausiid shrimp; (2) collagenases from various sources; (3) caseinase from various sources; (4) chymotrypsin from various sources; (5) carboxypeptidase from various sources; (6) ceratinase from various sources; (7) enterokinase from various sources; (8) rennet from various sources, etc. Enzymes that can be used together with MAP for melanin treatment are not limited to the enzymes above.

According to the present invention, MAP can be combined with an enzyme for melanin treatment, and the manner of use may comprise: (1) spray the enzyme first to decompose the corneous layer on the skin surface, then spray the enzyme again, and immediately spray MAP for them to work together for a period of time; (2) spray MAP first, and then spray the enzyme for them to work together for a period of time; (3) mix MAP with the enzyme for a period of time, and then spray it for use; (4) spray the enzyme first, and then spray MAP for them to work together for a period of time.

According to the present invention, the way in which MAP and an enzyme form a product may comprise: (1) MAP and the enzyme are in different packagings: use separately, or mixes them prior to use by the user; (2) a mixture of hydrolyzed MAP peptides: MAP is prepared, by using the above various enzymes, into a mixture of hydrolyzed peptides, use heating and other means to terminate the enzyme activity to form a product for direct use; (3) single hydrolyzed MAP peptide: MAP is prepared, by using the above various enzymes, into a mixture of hydrolyzed peptides, use an isolation method, such as chromatography, to remove the enzyme, remove peptides that do not contain a dopa group and remove peptides with an undesired molecular weight, and obtain a single peptide product that only contains the dopa group for direct use.

According to the present invention, when used to treat melanin, the molar ratio of MAP to an enzyme is in a range of 0.1:1-100:1, preferably in a range of 1:1-50:1.

DETAILED DESCRIPTION OF THE PREFERRED EMBODIMENTS

Embodiments of the present invention comprise:
1. Use of MAP in treating and preventing melanin pigmentation.
2. The use of MAP according to Embodiment 1, wherein the MAP may be one or a mixture of several selected from the group consisting of subtypes mefp-1, mefp-2, mefp-3, mefp-4, mefp-5, mefp-6, the collagens pre-COL-P, pre-COL-D, pre-COL-NQ and the mussel feet matrix proteins PTMP and DTMP.
3. The use of MAP according to Embodiment 1, wherein the MAP concentration may be 0.1-15.0 mg/mL.
4. The use of MAP according to Embodiment 1, wherein the MAP may be a liquid formulation, a gel formulation, a lotion, a paste, a therapy patch, or a foam formulation in use.
5. The use of MAP according to Embodiment 1, wherein MAP in the final product may be in a range of pH 1.0-7.0, and in particular, in a range of pH 3.0-6.5.
6. The use of MAP according to any one of Embodiments 1-5, wherein the melanin pigmentation may be chloasma, freckles, melanosis and other chromatosis, skin cancers with melanoma as a representative, and chromatosis that is caused by exposure to the sun or skin diseases like acne.

7. The use of MAP according to Embodiment 1, wherein the MAP may be used independently or combined with an enzyme in use.

8. The use of MAP according to Embodiment 7, wherein the MAP may be used directly or after a micro wound surface is created first.

9. The use of MAP according to Embodiment 8, wherein the methods to create a micro wound surface may include: micro-needle (which can be made of silicon, silicon dioxide, cellulose, etc.), rolling needle (which can be made of stainless steel, titanium, polytetrafluoroethylene, etc.), laser (e.g. fractional laser).

10. The use of MAP according to Embodiment 7, wherein the enzyme may be: (1) trypsin from various sources, for example, trypsin extracted from cod pancreas, bull pancreas, pig pancreas, and euphausiid shrimp; (2) collagenases from various sources; (3) caseinase from various sources; (4) chymotrypsin from various sources; (5) carboxypeptidase from various sources; (6) ceratinase from various sources; (7) enterokinase from various sources; (8) rennet from various sources, etc.

11. The use of MAP according to Embodiment 7, wherein the manner of use of a combination of MAP and an enzyme may comprise: (1) spray the enzyme first to decompose the corneous layer on the skin surface, then spray the enzyme again, and immediately spray MAP for them to work together for a period of time; (2) spray MAP first, and then spray the enzyme for them to work together for a period of time; (3) mix MAP with the enzyme for a period of time, and then spray it for use; (4) spray the enzyme first, and then spray MAP for them to work together for a period of time.

12. The use of MAP according to Embodiment 7, wherein MAP and the enzyme may be in different packagings.

13. The use of MAP according to Embodiment 7, wherein the use of a combination of MAP and an enzyme may be a use in the form of a mixture of hydrolyzed MAP peptides.

14. The use of MAP according to Embodiment 7, wherein the use of a combination of MAP and an enzyme may be a use in the form of a single hydrolyzed MAP peptide.

15. The use of MAP according to Embodiment 7, wherein the molar ratio of MAP to an enzyme may be in a range of 0.1:1-100:1, preferably in a range of 1:1-50:1.

16. Use of MAP as an active ingredient in a composition for treatment and prevention of melanin pigmentation, wherein the composition is a liquid formulation, a gel formulation, a lotion, a paste, a therapy patch, or a foam formulation in use.

17. The use of MAP according to Embodiment 16, wherein the composition is a composition for external application on the skin.

18. Use of MAP as an active ingredient in a drug for treatment of melanin.

19. Use of MAP as an active ingredient in a medical device for treatment of melanin.

20. Use of MAP as an active ingredient in a cosmetic for treatment of melanin.

21. Use of MAP as an active ingredient in a disinfecting product for treatment of melanin.

22. Use of MAP as an active ingredient in a healthcare product or food for treatment of melanin.

23. Use of MAP as an active ingredient in a household chemical for treatment of melanin.

24. The use of MAP according to any one of Embodiments 16-23, wherein MAP is combined with an enzyme in use.

25. A drug for treatment of melanin pigmentation, comprising MAP and a pharmaceutically acceptable carrier, wherein the MAP concentration is 0.1-15.0 mg/mL.

26. A medical device for treatment of melanin pigmentation, comprising MAP and a carrier acceptable in the field of medical devices, wherein the MAP concentration is 0.1-15.0 mg/mL.

27. A cosmetic for treatment of melanin pigmentation, comprising MAP and a carrier acceptable in the field of cosmetics, wherein the MAP concentration is 0.1-15.0 mg/mL.

28. A disinfecting product for treatment of melanin pigmentation, comprising MAP and a carrier acceptable in the field of disinfecting products, wherein the MAP concentration is 0.1-15.0 mg/mL.

29. A healthcare product or food for treatment of melanin pigmentation, comprising MAP and a carrier acceptable in the field of healthcare products or foods, wherein the MAP concentration is 0.1-15.0 mg/mL.

30. A household chemical for treatment of melanin pigmentation, comprising MAP and a carrier acceptable in the field of household chemicals, wherein the MAP concentration is 0.1-15.0 mg/mL.

31. The drug according to any one of Embodiments 25-30, further comprising an enzyme.

The present invention will be further described below with reference to specific embodiments. It should be noted that, when a drug, medical device, cosmetic, disinfecting product, healthcare product or food, or household chemical formed from MAP or various formulations of MAP according to the present invention is applied on a subject, it can be used for the indications described above and exhibits the functions described above. All formulations within the scope of the present invention have been tested, and only a small portion thereof are described below in the embodiments for the purpose of description; however, they shall not be construed as limitations to the present invention.

Unless otherwise specifically described, all reagents used in the present invention are commercially available on the market.

Example 1: Use of MAP Gel Cosmetic in Treatment of Chloasma

Mix an MAP solution with polyvinyl alcohol, hydroxypropyl cellulose, and glycerin at a mass ratio of 2:2:1:2 to obtain an MAP gel cosmetic with an MAP concentration of 3 mg/g.

Gather 10 patients with chloasma. It is required that the selected patients have the chin affected and the color of the patches is dark brown. They are diagnosed by dermatologists and then join the groups for test. Apply the above MAP gel cosmetic at the affected part once per day, and evenly apply the gel on the surface of the affected part each time. Measure the pigment value of the affected part using a pigment measurement instrument every 10 days. For the 10 patients, the pigment value of the affected part decreases by 9% at 50 days after application of the MAP gel cosmetic (see Table 1), proving that long-term use of the MAP product can reduce pigmentation at the position of chloasma.

TABLE 1

| | |
|---|---|
| Average pigment value of the affected part at Day 0 | 308 ± 10.7 |
| Average pigment value after 10 days of use | 303.4 ± 9.9 |
| Average pigment value after 20 days of use | 299.2 ± 9.5 |
| Average pigment value after 30 days of use | 293.6 ± 8.2 |
| Average pigment value after 40 days of use | 286.6 ± 5.8 |
| Average pigment value after 50 days of use | 280.6 ± 6.8 |

Example 2: Use of MAP Household Chemical Lotion in Treatment of Chloasma

Mix an MAP solution with propanediol and glycerin at a mass ratio of 2:2:1 to obtain an MAP household chemical lotion with an MAP concentration of 1.5 mg/g.

Gather 10 patients with chloasma. It is required that the selected patients have the chin affected and the color of the patches is dark brown. They are diagnosed by dermatologists and then join the groups for test. Apply the above MAP household chemical lotion at the affected part two times per day, and evenly apply the household chemical lotion on the surface of the affected part each time. Measure the pigment value of the affected part using a pigment measurement instrument every 10 days. For the 10 patients, the pigment value of the affected part decreases by 7.3% at 50 days after application of the MAP household chemical lotion (see Table 2), proving that long-term use of the MAP product can reduce pigmentation at the position of chloasma.

TABLE 2

| | |
|---|---|
| Average pigment value of the affected part at Day 0 | 316.0 ± 13.6 |
| Average pigment value after 10 days of use | 313.8 ± 9.3 |
| Average pigment value after 20 days of use | 309.4 ± 7.8 |
| Average pigment value after 30 days of use | 302.3 ± 7.2 |
| Average pigment value after 40 days of use | 298.6 ± 6.9 |
| Average pigment value after 50 days of use | 293.9 ± 8.2 |

Example 3: Use of MAP Liquid Medical Device in Treatment of Chloasma

Take 1 mL of an MAP solution with concentration at 20.0 mg/mL, add 9 mL of 0.1% citric acid solution, and prepare an aqueous solution with the MAP concentration at 2.0 mg/mL. Take 1.0 mg cod enzyme, and add 1.0 mL deionized water to prepare a solution with a concentration of 1.0 mg/mL.

Gather 30 patients with chloasma diagnosed by dermatologists for test. The patients have brown patches at the affected part.

The selected patients are randomly divided into three groups. For the first group marked as Group A, apply a commercially available spot-removing liquid at the affected part. For the second group marked as Group B, spray the above MAP liquid medical device at the affected part; for the third group marked as Group C, spray a composition of the MAP liquid medical device and an enzyme at the affected part, and in use, spray MAP first, and then spray the enzyme formulation. There are three drug administrations per day for all the three groups, and the dose is sufficient for the drugs to be evenly applied at the affected part. Prior to use, measure the melanin value of the affected part and the melanin value of areas surrounding the affected part and having no colored patches. Measure the melanin value of the affected part every 10 to 30 days, and calculate the rate of melanin change at the affected part (see Table 3 for results).

The rate of melanin change is calculated using the following equation:

(melanin value before use−melanin value after use)/
(melanin value before use−melanin value of a
normal position)×100%

TABLE 3

| Use time (d) | Rate of melanin change for Group A (%) | Rate of melanin change for Group B (%) | Rate of melanin change for Group C (%) |
|---|---|---|---|
| 10 | 0.6 ± 0.2 | 2.6 ± 0.4 | 8.3 ± 1.9 |
| 30 | 1.2 ± 0.3 | 5.8 ± 1.2 | 16.9 ± 2.7 |
| 60 | 4.3 ± 0.8 | 9.6 ± 1.8 | 20.6 ± 3.1 |
| 90 | 5.2 ± 1.6 | 13.7 ± 2.5 | 28.2 ± 2.8 |

The results show that compared with the commercially available spot-removing product, after 90 days of using the MAP liquid medical device, the rate of pigment value change at the affected part is more than one times, and the spot-removing effect is better than that of the commercially available product. After 90 days of using a combination of the MAP liquid medical device and an enzyme, the rate of pigment value change at the affected part reaches up to 28.2%, which achieves a significant effect on improving chloasma at the affected part. Moreover, compared with the use of the MAP product alone, the combined use of the MAP product and an enzyme increases the rate of pigment value change at the affected part by one time, which is more favorable for treatment of chloasma.

Example 4: Use of MAP Hydrogel Cosmetic in Treatment of Chloasma

Take 10 g sodium carboxymethyl cellulose, add 20 mL deionized water, place in a bath at 90□ for 30 min. until complete dissolution to obtain a gel matrix, separately take 2.5 mL of an MAP solution with concentration at 10.0 mg/mL, add it into the gel matrix while stirring, and mix homogeneously to form an MAP hydrogel cosmetic, wherein the MAP concentration is 1.1 mg/mL. Take 1.0 mg cod enzyme, and add 1.0 mL deionized water to prepare a solution with a concentration of 1.0 mg/mL.

Gather 20 patients with chloasma diagnosed by dermatologists for test. The patients have brown patches at the affected part.

For the selected patients, spray the above MAP hydrogel cosmetic at the affected part, and in use, spray the MAP hydrogel cosmetic first, and then spray the enzyme formulation, three times per day. Prior to use, measure the melanin value of the affected part and the melanin value of areas surrounding the affected part and having no colored patches. Measure the melanin value of the affected part every 10 to 30 days, and calculate the rate of melanin change at the affected part (see Table 4 for results).

The rate of melanin change is calculated using the following equation:

(melanin value before use−melanin value after use)/
(melanin value before use−melanin value of a
normal position)×100%

TABLE 4

| Use time (d) | Rate of melanin change (%) |
|---|---|
| 10 | 9.6 ± 1.6 |
| 30 | 18.2 ± 1.9 |
| 60 | 29.6 ± 2.7 |
| 90 | 38.4 ± 1.8 |

The results show that After 10 days of using the MAP hydrogel cosmetic and the enzyme, the pigment value at the affected part has begun to decrease, and along with the extended use time, the rate of the pigment value change at the affected part increases. As of 90 days of use, the pigment change at the affected part is more than ⅓. The MAP product according to the present invention can mitigate pigmentation at the position of chloasma, and can be used for treatment of chloasma.

Example 5: Use of MAP Liquid Drug in Treatment of Freckles

Take 1 mL of an MAP solution with concentration at 10.0 mg/mL, add 9 mL of 0.1% citric acid solution, and prepare a liquid drug with the MAP concentration at 1.0 mg/mL. Take 1.0 mg trypsin, and add 1.0 mL deionized water to prepare a solution with a concentration of 1.0 mg/mL.

Gather 20 patients with freckles diagnosed by dermatologists for test. The patients have brown patches at the affected part.

For the selected patients, spray the above MAP liquid drug at the affected part, and in use, spray the MAP liquid drug first, and then spray the enzyme formulation, three times per day. Prior to use, measure the melanin value of the affected part and the melanin value of areas surrounding the affected part and having no colored patches. Measure the melanin value of the affected part every 10 to 30 days, and calculate the rate of melanin change at the affected part (see Table 5 for results).

The rate of melanin change is calculated using the following equation:

(melanin value before use−melanin value after use)/
(melanin value before use−melanin value of a
normal position)×100%

TABLE 5

| Use time (d) | Rate of melanin change (%) |
|---|---|
| 10 | 6.4 ± 1.4 |
| 30 | 21.6 ± 2.8 |
| 60 | 28.7 ± 2.9 |
| 90 | 35.2 ± 3.6 |

The results show that After 10 days of using the MAP liquid drug and the enzyme, the pigment value at the affected part has begun to decrease, and along with the extended use time, the rate of the melanin change at the affected part increases. As of 90 days of use, the pigment change at the affected part reaches up to 35.2%, proving that the MAP product according to the present invention can mitigate pigmentation for patients with freckles, and can be used for treatment of freckles.

Example 6: Use of MAP Household Chemical Lotion in Treatment of Freckles

Mix propanediol and propanetriol at a ratio of 1:1 to obtain a lotion matrix, separately take 2.5 mL of an MAP solution with concentration at 10.0 mg/mL, add it into the lotion matrix while stirring, and mix homogeneously to form an MAP household chemical lotion, wherein the MAP concentration is 3.0 mg/mL.

Gather 30 patients with freckles diagnosed by dermatologists for test. The patients have brown patches at the affected part.

The selected patients are randomly divided into three groups. For the first group marked as Group A, a commercially available spot-removing lotion is applied. For the second group marked as Group B, directly apply the above MAP household chemical lotion at the affected part; for the third group marked as Group C, first use micro-needle to create a micro-wound surface at the affected part, and then apply the MAP household chemical lotion at the affected part. There are three drug administrations per day for all three groups, and the dose is sufficient for the drug to be evenly applied at the affected part. Prior to use, measure the melanin value of the affected part and the melanin value of areas surrounding the affected part and having no colored patches. After using MAP, measure the melanin value of the affected part every 10 to 30 days, and calculate the rate of melanin change at the affected part (see Table 6 for results).

The rate of melanin change is calculated using the following equation:

(melanin value before use−melanin value after use)/
(melanin value before use−melanin value of a
normal position)×100%

TABLE 6

| Use time (d) | Rate of melanin change for Group A (%) | Rate of melanin change for Group B (%) | Rate of melanin change for Group C (%) |
|---|---|---|---|
| 10 | 0.5 ± 0.3 | 3.9 ± 0.9 | 11.3 ± 2.6 |
| 30 | 1.1 ± 0.4 | 7.2 ± 1.6 | 28.5 ± 2.9 |
| 60 | 3.9 ± 0.7 | 11.6 ± 1.7 | 34.8 ± 3.8 |
| 90 | 5.0 ± 1.2 | 16.7 ± 2.4 | 42.6 ± 3.1 |

The results show that compared with the commercially available product, after 90 days of using the MAP household chemical lotion, the rate of melanin change is increased three times. After 90 days of using a combination of the MAP household chemical lotion and an enzyme, the rate of pigment value change at the affected part reaches up to 42.6%, which achieves a significant effect on improving freckle pigmentation at the affected part. Moreover, compared with the use of the MAP product alone, the combined use of the MAP product and an enzyme increases the rate of pigment value change at the affected part 2.5 times, which is more favorable for treatment of freckles.

Example 7: Use of MAP Lotion Cosmetic in Treatment of Melanosis

Mix MAP freeze-dried powder with gelatin, isinglass, and glycerin at a ratio of 3:1:1:0.5 to form an MAP lotion cosmetic, wherein the MAP concentration is 5.5 mg/mL.

Gather 12 patients with melanosis diagnosed by dermatologists. The patients use the above MAP lotion cosmetic twice a day at an amount capable of completely covering the testing area for 90 days in a row.

Measure the pigment situation of the affected part using a pigment measurement instrument. After 20 days of continuous use, the average pigment value of the affected part begins to decrease to around 96% of the initial value. At 90 days, the pigment value of the affected part decreases to 82.6% of the initial value (see Table 7), proving that the use of the MAP product according to the present invention can decrease pigmentation in melanosis.

TABLE 7

| | |
|---|---|
| Average pigment value of the affected part at Day 0 | 328.0 ± 23.7 |
| Average pigment value after 20 days of use | 317.7 ± 19.5 |
| Average pigment value after 40 days of use | 303.4 ± 15.8 |
| Average pigment value after 60 days of use | 292.6 ± 16.9 |
| Average pigment value after 80 days of use | 285.9 ± 18.1 |
| Average pigment value after 90 days of use | 271.2 ± 28.8 |

Example 8: Use of MAP Gel Healthcare Product in Treatment of Melanosis

Mix an MAP solution with gelatin and glycerin at a ratio of 1:1:1 to form an MAP gel healthcare product, wherein the MAP concentration is 10.0 mg/mL.

Gather 12 patients with melanosis diagnosed by dermatologists. The patients use the above MAP gel healthcare product twice a day at a dose capable of completely covering the testing area for 90 days in a row.

Measure the pigment situation of the affected part using a pigment measurement instrument. After 20 days of continuous use, the average pigment value of the affected part begins to decrease to 96% of the initial value. At 90 days, the pigment value of the affected part decreases to 80% of the initial value (see Table 8), proving that the use of the MAP product according to the present invention can decrease pigmentation in melanosis.

TABLE 8

| | |
|---|---|
| Average pigment value of the affected part at Day 0 | 353.3 ± 43.1 |
| Average pigment value after 20 days of use | 341.7 ± 36.4 |
| Average pigment value after 40 days of use | 316.6 ± 25.6 |
| Average pigment value after 60 days of use | 300.3 ± 24.8 |
| Average pigment value after 80 days of use | 290.9 ± 19.6 |
| Average pigment value after 90 days of use | 282.2 ± 24.9 |

Example 9: Use of MAP Liquid Healthcare Product in Treatment of Melanosis

Take 10 mL of an MAP solution with concentration at 10.0 mg/mL add 10 mL of 0.001% acetic acid solution, and prepare an aqueous solution with the MAP concentration at 5.0 mg/mL.

Gather 12 patients with melanosis diagnosed by dermatologists for test. Use the laser micro-wound technology to create micro-wound surfaces on the testing surfaces of the patients, and then the above MAP liquid healthcare product is used twice per day at an amount capable of completely covering the testing area for 90 days in a row.

Prior to use, measure the melanin value of the affected part and the melanin value of areas surrounding the affected part and having no colored patches. Measure the melanin value of the affected part every 10 to 30 days, and calculate the rate of melanin change at the affected part (see Table 9 for results).

The rate of melanin change is calculated using the following equation:

(melanin value before use−melanin value after use)/
(melanin value before use−melanin value of a
normal position)×100%

TABLE 9

| Use time (d) | Rate of melanin change (%) |
|---|---|
| 10 | 4.2 ± 1.1 |
| 30 | 25.6 ± 3.8 |
| 60 | 37.1 ± 3.6 |
| 90 | 42.2 ± 3.7 |

The results show that after using the MAP liquid healthcare product, the pigment value at the affected part has begun to decrease, and along with the extended use time, the rate of the melanin change at the affected part increases. As of 90 days of use, the pigment change at the affected part reaches up to 42.2%, proving that the MAP product according to the present invention can mitigate pigmentation for patients with melanosis, and can be used for treatment of melanosis.

Example 10: Use of MAP Hydrogel Medical Device in Treatment of Melanosis

Mix MAP, Carbomer and propanediol at a mass ratio of 1:1:2 to obtain an MAP hydro-lotion medical device, wherein the MAP concentration is 2.5 mg/mL.

Gather 12 patients with melanosis diagnosed by dermatologists for test. Use the rolling needle micro-wound technology to create micro-wound surfaces on the testing surfaces of the patients, and then the MAP hydrogel medical device is used twice per day at an amount capable of completely covering the testing area for 90 days in a row.

Prior to use, measure the melanin value of the affected part and the melanin value of areas surrounding the affected part and having no colored patches. After using MAP, measure the melanin value of the affected part every 10 to 30 days, and calculate the rate of melanin change at the affected part (see Table 10 for results).

The rate of melanin change is calculated using the following equation:

(melanin value before use−melanin value after use)/
(melanin value before use−melanin value of a
normal position)×100%

TABLE 10

| Use time (d) | Rate of melanin change (%) |
|---|---|
| 10 | 10.3 ± 1.6 |
| 30 | 23.6 ± 3.1 |
| 60 | 31.8 ± 2.8 |
| 90 | 39.2 ± 3.5 |

The results show that after 10 days of using the MAP hydrogel medical device, the pigment value at the affected part has begun to decrease, and along with the extended use time, the rate of the melanin change at the affected part increases. As of 90 days of use, the pigment change at the affected part reaches up to 39.2%, proving that the MAP product according to the present invention can mitigate pigmentation for patients with melanosis, and can be used for treatment of melanosis.

Example 11: Use of MAP Liquid Cosmetic in Treatment to Inhibit Melanin Pigmentation after Burns Take an MAP solution, add 0.01% citric acid to adjust pH to 4.0 and obtain an MAP liquid cosmetic, wherein the MAP concentration is 10.0 mg/mL.

Gather five patients in the healing phase after burns, the burn surface area of the patients is greater than 2% of the human body surface area, and the subjects join the test after voluntarily signing an Informed Consent Form. The patients use the above MAP liquid cosmetic three times per day at an amount each time capable of evenly covering the affected part. During the test, an adjacent area of the same body is selected as the control, namely two areas of the same body are selected, one of which is applied with the above MAP liquid cosmetic (the test group), and the other one thereof is treated according to a normal procedure (the control group). At Day 0, Day 7 and Day 14 of the use, determine pigment for the test group, the control group and the healthy skin, respectively (see Table 11). After 14 days of treatment, no obvious melanin pigmentation is observed on the skin recovered from the burn by using the MAP liquid cosmetic, while obvious pigmentation is observed on the skin that did not use the MAP liquid cosmetic.

TABLE 11

| | Pigment of healthy skin | Pigment of skin in the test group | Pigment of skin in the control group |
|---|---|---|---|
| Day 0 | 138.7 ± 5.8 | 139.6 ± 6.1 | 139.6 ± 6.1 |
| Day 7 | 138.7 ± 5.8 | 142.6 ± 4.3 | 157.4 ± 5.5 |
| Day 14 | 138.7 ± 5.8 | 145.2 ± 4.9 | 170.2 ± 6.0 |

The invention claimed is:

1. A method for treating melanin pigmentation selected from the group consisting of chloasma, freckles, melanosis and chromatosis, the method comprising
administering to an individual in need thereof an effective amount of a composition comprising a mussel adhesive protein (MAP), wherein the MAP comprises one or more of the sub-types selected from the group consisting of *M. edulis* foot protein 1 (mefp-1), mefp-2, mefp-3, mefp-4, mefp-5 and mefp-6, wherein said administering treats melanin pigmentation.

2. The method according to claim 1, wherein the MAP comprises mefp-1.

3. The method according to claim 1, wherein the MAP is present in the composition at a concentration of 0.1 to 15.0 mg/ml.

4. The method according to claim 1, wherein the composition is a liquid formulation, a gel formulation, a lotion, a paste, a foam formulation, or in the form of a therapy patch.

5. The method according to claim 1, wherein the composition has a pH in the range of 1.0 to 7.0.

6. The method according to claim 5, wherein the composition has a pH in the range of 3.0 to 6.5.

7. The method according to claim 1, further comprising administering an enzyme to the individual.

8. The method according to claim 1, wherein the enzyme is selected from the group consisting of trypsin, a collagenase, a caseinase; chymotrypsin, a carboxypeptidase, a ceratinase, an enterokinase, and rennet.

9. The method according to claim 8, wherein the enzyme is trypsin.

10. The method according to claim 7, wherein said administering the composition and said administering the enzyme comprises:
    (a) spraying a composition comprising the enzyme onto the skin surface to decompose the corneous layer on the skin surface, repeating said spraying the composition comprising the enzyme onto the skin surface, and then spraying the composition comprising the MAP onto the skin surface; or
    (b) spraying the composition comprising the MAP onto the skin surface, and then spraying a composition comprising the enzyme onto the skin surface; or
    (c) mixing the composition comprising the MAP with a composition comprising the enzyme and then spraying the mixture onto the skin surface; or
    (d) spraying a composition comprising the enzyme onto the skin surface, and then spraying the composition comprising the MAP onto the skin surface.

11. The method according to claim 10, wherein the composition comprising the MAP and the composition comprising the enzyme are provided in different packages.

12. The method according to claim 7, wherein the MAP is provided in the form of a mixture of hydrolyzed MAP peptides or the form of a single hydrolyzed MAP peptide.

13. The method according to claim 7, wherein the molar ratio of MAP to the enzyme is in the range of 0.1:1-100:1.

14. The method according to claim 13, wherein the molar ratio is in the range of 1:1-50:1.

15. The method according to claim 1, wherein the composition is suitable for external skin application.

16. The method according to claim 1, wherein the composition is a medicine, a cosmetic preparation, a disinfecting product, a healthcare product, a food or a household chemical.

* * * * *

UNITED STATES PATENT AND TRADEMARK OFFICE
CERTIFICATE OF CORRECTION

PATENT NO. : 10,675,327 B2
APPLICATION NO. : 15/742969
DATED : June 9, 2020
INVENTOR(S) : Jan Christer Janson and Min Gao Page 1 of 1

It is certified that error appears in the above-identified patent and that said Letters Patent is hereby corrected as shown below:

In the Claims

In Claim 8 at Column 15, Line 40, delete "according to claim 1" and insert in its place --according to claim 7--.

Signed and Sealed this
First Day of September, 2020

Andrei Iancu
*Director of the United States Patent and Trademark Office*